(12) United States Patent
Pohl et al.

(10) Patent No.: US 8,399,702 B2
(45) Date of Patent: Mar. 19, 2013

(54) PROCESS FOR THE PRODUCTION OF AROMATIC DIISOCYANATES IN THE GAS

(75) Inventors: Fritz Pohl, Brunsbüttel (DE); Klaus Biskup, Leverkusen (DE); Rainer Bruns, Leverkusen (DE); Friedhelm Steffens, Leverkusen (DE); Lars Padeken, Düsseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 814 days.

(21) Appl. No.: 12/313,469

(22) Filed: Nov. 20, 2008

(65) Prior Publication Data

US 2009/0149672 A1  Jun. 11, 2009

(30) Foreign Application Priority Data

Nov. 22, 2007 (DE) .......................... 10 2007 056 511

(51) Int. Cl.
*C07C 263/00* (2006.01)
(52) U.S. Cl. ....................................................... 560/347
(58) Field of Classification Search .................. None
See application file for complete search history.

(56) References Cited

U.S. PATENT DOCUMENTS

| | | | |
|---|---|---|---|
| 4,847,408 A | 7/1989 | Frosch et al. | |
| 5,391,683 A | 2/1995 | Joulak et al. | |
| 5,449,818 A * | 9/1995 | Biskup et al. | 560/347 |
| 5,516,935 A | 5/1996 | Bischof et al. | |
| 5,609,735 A | 3/1997 | Hetzel et al. | |
| 5,633,396 A | 5/1997 | Bischof et al. | |
| 6,706,913 B2 | 3/2004 | Leimkuehler et al. | |
| 6,803,482 B2 | 10/2004 | Jenne et al. | |
| 6,838,578 B2 | 1/2005 | Leimkuehler et al. | |
| 6,930,199 B2 | 8/2005 | Meyn et al. | |
| 6,974,880 B2 | 12/2005 | Biskup et al. | |
| 7,084,297 B2 | 8/2006 | Woelfert et al. | |
| 2003/0013909 A1 | 1/2003 | Leimkuhler et al. | |
| 2003/0069441 A1 | 4/2003 | Leimkuhler et al. | |
| 2003/0216597 A1 | 11/2003 | Jenne et al. | |
| 2004/0167354 A1 | 8/2004 | Biskup et al. | |
| 2005/0070734 A1 | 3/2005 | Woelfert et al. | |
| 2005/0113601 A1 | 5/2005 | Herold et al. | |
| 2005/0137417 A1 | 6/2005 | Meyn et al. | |
| 2006/0025556 A1* | 2/2006 | Koch et al. | 528/44 |
| 2007/0043233 A1 | 2/2007 | Sanders et al. | |
| 2008/0146834 A1 | 6/2008 | Pohl et al. | |

FOREIGN PATENT DOCUMENTS

WO  2007028715 A1  3/2007

* cited by examiner

*Primary Examiner* — Sudhakar Katakam
(74) *Attorney, Agent, or Firm* — Lyndanne M. Whalen

(57) ABSTRACT

Aromatic diisocyanates are produced by reacting in the gas phase the corresponding primary aromatic diamine with phosgene. The phosgene and the primary aromatic diamine are reacted within a mean residence time of from 0.05 to 15 seconds. The aromatic diamine used contains less than 0.05 mole % overall of aliphatic amine containing no keto groups, per mole of primary amino groups.

15 Claims, No Drawings

PROCESS FOR THE PRODUCTION OF AROMATIC DIISOCYANATES IN THE GAS

BACKGROUND OF THE INVENTION

The present invention relates to a process for the production of a primary aromatic diisocyanate by reacting the corresponding primary aromatic diamine with phosgene in the gaseous phase, in which phosgene and the primary aromatic diamine are reacted within a mean residence time of from 0.05 to 15 seconds and the primary aromatic diamine used contains less than 0.05 mole % of aliphatic amine groups per mole of primary amino groups and no keto groups are present in any aliphatic amine which is present.

Various processes for the production of diisocyanates by reacting diamines with phosgene in the gaseous phase, particularly the phosgenation of aliphatic diamines in the gaseous phase, have already been described in detail in the prior art.

EP-B1-0 289 840 discloses a process for the production of diisocyanates of the general formula OCN—R—NCO, in which R denotes a (cyclo)aliphatic hydrocarbon radical with up to 15 carbon atoms, by phosgenation of the corresponding diamines of the general formula $H_2N$—R—$NH_2$ in the gaseous phase. In this disclosed process, the diamines in the vapor phase, optionally diluted with an inert gas or with the vapors of an inert solvent, and phosgene are heated separately to temperatures from 200° to 600° C. and are continuously reacted in a cylindrical reactor/reaction zone without any moving parts heated to 200° to 600° C. while maintaining a turbulent flow in the reactor/reaction zone. The gaseous mixture leaving the reactor/reaction zone is passed through an inert solvent which is maintained at a temperature above the decomposition temperature of the carbamyl chloride corresponding to the diamine. The diisocyanate dissolved in the inert solvent is subjected to a distillative working-up.

The process described in EP-B1-0 289 840 has been repeatedly modified in further publications both with respect to its range of application and also with respect to apparatus. EP-B1-0 749 958 discloses the reaction of (cyclo)aliphatic triamines with three primary amino groups in the gaseous phase in a tubular reactor at 200° to 600° C. EP-B1-1 078 918 discloses the application of the basic principles of EP-B1-0 289 840 to the gas phase phosgenation of (cyclo)aliphatic diamines with two primary amino groups in the 1,2- or 1,3-position with respect to one another. EP-B1 1 275 639 and EP-B1 275 640 disclose special reactor configurations for an improved intermixing of the reactants fed to the reactor/reaction zone.

The reaction of aromatic diamines with phosgene in the gaseous phase to form the corresponding diisocyanates is also described in the literature.

EP-B1-0 593 334 discloses a process for the production of aromatic diisocyanates in the gaseous phase, in which a tubular reactor is used. In EP-B1-0 593 334 a mixing of the educts without stirring is achieved by a constriction of the walls. The reaction is carried out in the temperature range from 250° to 500° C. The process is however problematic because the mixing of the educt streams solely via a constriction of the tubular wall gives poor results compared to the use of a mixing device. Poor mixing normally leads to formation of an undesirably high amount of solids.

EP-A-0 699 657 discloses a process for the production of aromatic diisocyanates in the gaseous phase in a mixed reactor, which comprises a first homogenizing zone and a second, essentially piston flow downstream zone. Nevertheless, in this process problems also arise due to the formation of solids which block the mixing and reaction equipment and reduce the yield.

There have been a number of attempts to minimize the formation of solids, particularly in the reaction of aromatic diamines with phosgene in the gaseous phase, in order to allow an industrial scale phosgenation of aromatic diamines in the gaseous phase.

EP-B1-0 570 799 discloses a process for the production of aromatic diisocyanates in which the reaction of the appropriate diamine with phosgene is carried out in a tubular reactor above the boiling point of the diamine and within a mean residence time of 0.5 to 5 seconds. According to the teaching of EP-B1-0 570 799, homogenization of the flow in the reaction zone is necessary in order to minimize the undesirable formation of solids and to prevent a back mixing of the components in the reactor/reaction zone. In the process described in EP-B1-0 570 799, the mean deviation from the mean residence time is less than 6%. The maintenance of this residence time is achieved if the reaction is carried out in a tubular flow which is characterised either by a Reynolds number of above 4 000 or a Bodenstein number of above 100.

Measures for averaging out the flow conditions are also the subject-matter of EP-B1-1 362 847. EP-B1-1 362 847 discloses a process for the production of aromatic diisocyanates in the gaseous phase in which the reaction conditions in tubular reactors are improved. In this process, flow-related measures such as the averaging out and centering of the educt streams are used to avoid temperature fluctuations over time and an asymmetry in the temperature distribution. It is temperature fluctuation and asymmetry in the temperature distribution which EP-B1-1 362 847 teaches to be responsible for caking and blockages in the reactor and thus to a reduced service life of the reactors.

EP-A1-1 449 826 teaches that in the reaction of the aromatic diamines with phosgene in the gaseous phase, the reaction of the phosgene with the diamine to form the diisocyanate competes with the subsequent reaction of the diamine with the diisocyanate to form the corresponding urea oligomer. An improved mixing of the phosgene and diamine educts with a simultaneous avoidance of back flow due to eddy effects in the tubular reactor is taught to increase the selectivity of the diisocyanate formation and reduce the formation of urea. In this way, according to the teaching of EP-A1-1 449 826, the amount of condensation product in the tubular reactor can be reduced. The deposition of condensation product on the reactor wall leads to a reduction of the free tubular cross-section, to a gradual increase in pressure in the reactor, and ultimately determines the lifetime of the process. Similarly, EP-A1-1 526 129, DE-A-103 59 627 and WO 2007/028 751 A disclose apparatus-type solutions for improving the mixing of the educts. Flow technology measures to generate angular momentum are taught in EP-A-1 526 129. Concentrically arranged annular nozzles with singular amine feed are disclosed in DE-A-103 59 627, the use a of multiple amine feed is disclosed in WO 2007/028 751 A. Multiple amine nozzles arranged parallel to the axis of a tubular reactor are taught in EP-A1-1 449 826.

WO 2003/045 900 A deals comprehensively with the question of adjusting and controlling the temperature in the production of isocyanates on an industrial scale by a gas phase phosgenation. As is disclosed in WO 2003/045 900 A, in the known processes for the gas phase phosgenation that employ a cylindrical reaction zone, two possibilities for the technical realization are available. The first alternative is to carry out the reaction in a single tubular section, the diameter of which has to be adapted to the production capacity of the plant.

According to WO 2003/045 900 A, this concept is disadvantageous for very large production plants because an accurate temperature control of the reaction flows in the core of the flow can no longer be realized by heating/cooling the wall of the tube. Local temperature inhomogeneities can, if the temperature is too high, lead to decomposition of the product, while if the temperature is too low, this temperature can lead to an insufficient conversion of the educts to form the desired isocyanate. The second alternative, to subdivide the reacting mixture into individual partial streams, which are then parallel led through smaller, individual tubes, the temperatures of which can be better controlled due to their smaller diameter is also regarded as a disadvantage by WO 2003/045 900 A. According to WO 2003/045 900 A, the disadvantage of this process variant is that it is relatively susceptible to blockages unless the volume flow through each individual tube is regulated. According to the teaching of WO 2003/045 900 A, the outlined disadvantages can be circumvented advantageously for example with regard to a long or on-stream time of the production plant, by continuous phosgenation of amines in the gaseous phase in a non-cylindrical reaction channel, preferably a plate reactor, which preferably has a height that allows temperature control of the reactants and has a width which is at least twice the height. As WO 2003/045 900 A also discloses, the height of the reaction channel is in general not restricted and the reaction can take place in a reaction channel with a height of, for example, 40 cm. However, there should be a better heat exchange with the reactor walls. Accordingly, WO 2003/045 900 A teaches that the reaction should be carried out in reaction channels of low height.

WO 2007/028 715 A teaches that amines can be converted in a gas phase phosgenation to the corresponding isocyanates if certain requirements are satisfied. Amines which can be converted to the gaseous phase without any significant decomposition are particularly suitable. According to the teaching of WO 2007/028 715 A, suitable amines are those which, during the duration of the reaction, decompose to an extent of 2 mole % or less, more preferably 1 mole % or less and most preferably 0.5 mole % or less under the reaction conditions.

EP-A-1 754 698 teaches that the partial decomposition of the amines employed in the gaseous phase phosgenation to form ammonia has to be borne in mind not only during the reaction, but also has to be taken into account in vaporization of the amines. Ammonia formed by partial decomposition of the amines during vaporization not only reduces the yield, but in the subsequent phosgenation it also forms ammonium chloride deposits downstream in connected piping and apparatus. The plants then have to be cleaned relatively often, resulting in corresponding production losses.

Despite the attempts to optimize the reaction of aromatic amines with phosgene in the gaseous phase and thereby minimize the formation of solids that can be observed in the reaction of aromatic diamines with phosgene in the gaseous phase, there remains a need to improve the gas phase phosgenation of aromatic diamines to permit an industrial scale phosgenation of aromatic diamines in the gaseous phase.

SUMMARY OF THE INVENTION

The object of the present invention was to provide a simple and economical process for the production of aromatic diisocyanate(s) from the corresponding aromatic diamine(s) by phosgenation in the gas phase that ensures a technically advantageous conversion, in particular with regard to a high space-time yield and a low occurrence of interfering solids and the associated caking, deposits and blockages.

Surprisingly this object has been achieved by (1) reacting phosgene and the primary aromatic diamine(s) within a mean, hydrodynamic residence time of from 0.05 to 15 seconds and (2) using primary aromatic diamine(s) containing overall less than 0.05 mole % of aliphatic amine(s) per mole of primary amino groups and (3) ensuring that no keto groups are present in any aliphatic amine which may be present. It is aliphatic amines containing no keto groups which are believed to be largely responsible for the formation of solid deposits in the gas phase phosgenation.

DETAILED DESCRIPTION OF THE INVENTION

The present invention provides a process for the production of primary aromatic diisocyanate(s) by reacting the corresponding primary aromatic diamine(s) with phosgene in the gaseous phase, in which
a) phosgene and the primary aromatic diamine(s) are reacted within a mean residence time of 0.05 to 15 seconds, and
b) the primary aromatic diamine(s) employed contains overall less than 0.05 mole %, preferably less than 0.04 mole %, and most preferably from less than 0.001 mole % to 0.035 mole % of aliphatic amine(s) per mole of primary amino groups and no keto groups are present in any aliphatic amine which is present.

Aliphatic amines containing no keto groups include linear as well as branched aliphatic amines and also cycloaliphatic amines, which can optionally also be substituted or monounsaturated or polyunsaturated, so long as they contain no keto groups. Typical substituents are, for example, nitro, nitroso or Cl substituents.

The aliphatic amines containing no keto groups also include polynuclear or bridged cycloaliphatic amines, which can optionally also be substituted or monounsaturated or polyunsaturated so long as they contain no keto groups. The polynuclear or bridged cycloaliphatic amines can be bonded directly or can be bridged via one or more heteroatoms, in particular via one or more nitrogen atoms.

The term "moles of primary amino groups" means the sum total of the amino groups from the primary aromatic amines and from the aliphatic amines containing no keto groups.

The low content of aliphatic amines containing no keto groups in the aromatic diamines to be reacted in the desired gas phase phosgenation which is required in the present invention is all the more surprising because simultaneous phosgenation of aliphatic and aromatic primary amino groups is taught in the prior art. (See, e.g., DE-A 2249459, DE-A-198 28 510). Although the literature deals with the stability of the amines used in a gas phase phosgenation regarding their decomposition under de-amination, no information on the necessary relative stability of the formed isocyanates by the simultaneous use of both aromatic and (cyclo)aliphatic primary amino groups can be derived from the specified vaporization and reaction conditions. In particular, the prior art does not give any indication that the aliphatic amines containing no keto groups are a problem.

Although the process of the present invention is, in principle, suitable for the gas phase phosgenation of all aromatic diamines (for example, naphthalenediamines (NDA), in particular 1,5-NDA and 1,8-NDA; diamines of the diphenylmethane series (MDA), in particular 2,2'-MDA, 2,4'-MDA and 4,4'-MDA; and also toluenediamine (TDA), in particular 2,4-TDA and 2,6-TDA) that are identified in the prior art as stable under the reaction conditions (WO 2007/0 287 515 A), it is preferred to use toluene diamine as an isomer mixture together with phosgene in the gaseous phase to form the corresponding toluene diisocyanates. It is particularly preferred to use 2,4-/2,6-toluene diamine mixtures, most preferably of 2,4-/2,6-toluene diamine mixtures in isomer ratios of 80/20 and 65/35 in the process of the present invention.

The preferred use of the process according to the invention in the reaction of toluene diamine with phosgene in the gaseous phase is particularly important insofar as the industrial scale production of toluene diamine is specifically carried out by catalytic hydrogenation of dinitrotoluenes. The mixtures of isomeric dinitrotoluenes used are mainly obtained by nitrating toluene with nitric acid according to the mixed acid process (Ullmann's Enzyklopedie der technischen Chemie, 4$^{th}$ Ed. Vol, 7, p. 393ff, 1973, Verlag Chemie Weinheim/New York). In the hydrogenation, aside from the desired nitro group reduction, nuclear hydrogenations as well as further secondary reactions forming aliphatic or cycloaliphatic or polynuclear or bridged by-products containing primary amine groups also take place.

The process according to the invention preferably includes one or more of the following steps a)-d), most preferably all of steps a)-d):
  a) the aromatic diamine(s) in the vapor state, optionally diluted with an inert gas or with the vapors of an inert solvent, and phosgene are heated separately to temperatures of from 200° to 600° C. and are continuously mixed to obtain a reaction mixture,
  b) the reaction mixture formed in step a) is continuously led through a reactor/reaction zone while avoiding back mixing and is reacted therein in a mean residence time of from 0.05 to 15 seconds, thereby forming a gas mixture,
  c) the gas mixture leaving the reactor/reaction zone is cooled to condense the formed aromatic diisocyanate(s) at a temperature which is maintained above the decomposition temperature of the carbamyl chloride(s) corresponding to the reacted aromatic diamine(s), and
  d) non-condensed aromatic diisocyanate is separated from the gas mixture by washing with a wash liquid.

In step b), a reactor/reaction zone which preferably has a rotationally symmetrical geometry with a constant or increasing flow cross-sectional area in the flow direction of the reaction mixture is preferably used. A tubular reactor with a substantially constant or increasing flow cross-sectional area in the flow direction of the reaction mixture is preferably used as the reactor/reaction zone. In a further preferred embodiment, the reactor/reaction zone, preferably a tubular reactor, has sections of constant and increasing cross-sectional area in the flow direction.

A configuration of the reactor/reaction zone for use in the process of the present invention with a rotationally symmetrical geometry and a cascade-like and/or continuous change, in the flow direction, of the flow cross-sectional area has the advantage that the flow velocity along the axis of the reactor/reaction zone can be adjusted. A constant flow cross-sectional area in the flow direction leads to an acceleration of the flow due to the increase in volume during the phosgenation. The flow velocity of the reaction mixture over the length of the reactor can be kept constant by a suitably chosen enlargement of the flow cross-sectional area in the flow direction.

Preferably the reactor/reaction zone in step b) is charged according to the jet mixer principle with the components prepared and heated according to step a). In the jet mixer principle (Chemie-Ing.-Techn. 44, (1972), pp. 1055, FIG. 10) two educt streams A and B are fed to a rotationally symmetrical reaction space, the educt stream A being fed in through a central nozzle and the educt stream B being fed in through an annular space between the central nozzle and reactor wall. The flow velocity of the educt stream A is large compared to the flow velocity of the educt stream B. The result is a mixing of the reactants in the rotationally symmetrical reaction space, followed by their reaction. The intermixing of the components can be improved by flow technology measures such as those described, for example, in EP-B1-1 362 847 and EP-A1-1 526 129. Modifications of the basic principle, such as concentrically arranged annular nozzles with singular amine feed (DE-A-103 59 627) or a plurality of amine nozzles arranged parallel to the axis of a tubular reactor (EP-A1-1 449 826) can also be employed. It is likewise possible according to the teaching of WO 2007/028 751 A to feed the components through a concentrically arranged annular nozzle with simple or multiple amine feed into the reaction space. The above-described applications and the measures taught by them for improving mixing and the characteristic values required for this purpose are referred to here in particular.

The aromatic starting amine(s) is/are as a rule vaporized before the performance of the process according to the invention. The amine starting material is heated to a temperature of from 200° to 600° C., preferably from 225° to 500° C., most preferably from 250° to 450° C., and then fed (optionally diluted with an inert gas such as $N_2$, He, Ar or with the vapors of an inert solvent such as an aromatic hydrocarbon, optionally with halogen substituents, e.g., chlorobenzene or o-dichlorobenzene) to the reactor/reaction zone.

The vaporization of the aromatic starting amine(s) can be carried out in any of the known evaporation apparatuses. Preferably, evaporation systems are used in which a small working volume is fed at a high circulation rate over a falling-film evaporator. In this connection, the evaporation process is preferably assisted in order to minimize the thermal stress of the starting amine(s), optionally by feeding inert gas and/or vapors of an inert solvent. The use of microheat exchangers, as disclosed in EP-A-1 754 689, is however also possible. The aromatic diamine(s) in the vapor state can also contain amounts of non-vaporized droplets of aromatic diamine(s) (aerosol). Preferably, however, the aromatic diamine(s) in the vapor state contain substantially no droplets of non-vaporized aromatic diamine(s), in other words at most 0.5 mass % of the aromatic diamine, more preferably at most 0.05 mass % of the aromatic diamine, based on the total mass of the aromatic diamine, is present in the form of non-vaporized droplets and the remainder of the aromatic diamine is present in the vapor state. Most preferably, the aromatic diamine in the vapor state contains no droplets of non-vaporized aromatic diamine. After vaporization, the aromatic diamine in the vapor state, possibly diluted with inert gases or inert solvent vapors, is preferably brought to the desired operating temperature by using a post-heater.

The vaporization and superheating of the starting amine is preferably carried out in several stages, in order to avoid non-vaporized droplets entering the vaporous amine stream. Particularly preferred are multistage vaporization steps, in which droplet separators are incorporated between the vaporization and superheating systems and/or the vaporization apparatuses also perform the function of a droplet separator. Suitable droplet separators are described, for example, in "Droplet Separation", by A. Bürkholz, VCH Verlagsgesellschaft, Weinheim-New York-Basel-Cambridge, 1989. Particularly preferred are droplet separators that produce a small pressure drop. Most preferably, the vaporized aromatic diamine is heated to the desired operating temperature by a post-heater that also acts as a droplet separator. Preferably this post-heater has a liquid discharge system in order to ensure that the separator is constantly emptied. The service life of the reactor is significantly increased by producing a substantially droplet-free vaporous starting amine stream before entry to the reactor.

In the process of the present invention, it is advantageous to use phosgene in excess with respect to the amino groups. A molar ratio of phosgene to amino groups of from 1.1:1 to 20:1, preferably from 1.2:1 to 5:1 is normally used. Also, the phosgene is preferably heated to temperatures of 200° to 600° C. and is fed, optionally diluted with an inert gas (e.g., $N_2$, He, Ar) or with the vapors of an inert solvent (e.g., aromatic hydrocarbons, without or with halogen substitution, such as chlorobenzene or o-dichlorobenzene) to the reactor/reaction zone. The phosgene fed to the reactor/reaction zonce can also be diluted with HCl or CO.

In a preferred embodiment of the process of the present invention, the separately heated reactants are introduced into at least one reaction zone, mixed, and, taking account of suitable reaction times, reacted under adiabatic reaction conditions. The isocyanate is then condensed by cooling the gas stream. The cooling is carried out down to a temperature above the decomposition temperature of the corresponding carbamyl chloride (e.g., toluenediamine acid chloride in the case of TDA).

The necessary residence time for the reaction of the aromatic amino groups with the phosgene to form isocyanate is between 0.05 and 15 seconds, preferably between 0.1 and 10 seconds. The suitable residence time depends on the type of aromatic diamine that is used, the starting reaction temperature, the adiabatic temperature rise in the reactor/reaction zone, the molar ratio of used aromatic diamine and amino groups and phosgene, the pressure in the reactor/reaction zonce, and any dilution of the reactants with inert gases.

If for a given system (starting reaction temperature, adiabatic temperature rise, molar ratio of the reactants, diluent gas, employed aromatic diamine, pressure in the reactor/reaction zone), the minimum residence time for the complete reaction is exceeded by less than 20%, preferably by less than 10%, then the formation of secondary reaction products such as isocyanurates and carbodiimides from the formed aromatic diisocyanates can be largely avoided.

In the practical implementation of the process of the present invention, a deviation from the mean residence time (contact time) can occur due to the time required for mixing the reactants. As long as the reactants are not yet homogeneously mixed, still unmixed or partially mixed gas volumes in which no contact or no complete contact of the reactants has yet occurred are present in the reactor. The mixing of the reactants should therefore preferably take place within a time of from 0.01 to 0.3 second up to a degree of segregation of at least $10^{-1}$. The degree of segregation is a measure of the incompleteness of the mixing (See, for example, Chem.-Ing.-Techn. 44, (1972), pp. 1051ff; Appl. SCi. Res. (The Hague) A3 (1953), p. 279).

The methods for implementing short mixing times are in principle known. As already mentioned above, mixing equipment or mixing zones with moving or static mixing devices or nozzles are examples of suitable mixing equipment. Static mixers, such as are described for example in EP-A-1 362 847, EP-A-1 526 129 or EP-A-1 555 258, are preferred.

After mixing the reactants, the reaction mixture flows through the reactor/reaction zone. In this connection, preferably neither the mixing zone nor the reaction zone connected thereto include (a) heating surfaces which could give rise to a thermal stress resulting in secondary reactions such as isocyanurate or carbodiimide formation, or (b) cooling surfaces which could give rise to condensation resulting in deposits. The components are preferably reacted adiabatically. The adiabatic temperature rise in the reactor is then determined solely by the temperatures, the compositions and relative metered amounts of the educt streams, as well as the residence time in the reactor.

The flow through the reacto/reaction zone should preferably take place in the form of up to approximately 90% plug flow so that all parts of the volume of the flow have approximately the same flow time, resulting in the least possible further broadening of the residence time distribution between the reactants. The degree of realization of the ideal plug flow (with a mean deviation from the mean residence time=0) is described in flow technology by the Bodenstein number, Bo (Fitzer, Techn. Chemie, Springer 1989, pp. 288-295). In the process of the present invention, the Bodenstein number should preferably be at least 10, more preferably greater than 100, and most preferably greater than 250.

After completion of the phosgenation reaction in the reactor/reaction zone, in step c) the gas mixture continuously leaving the reactor/reaction zone, which preferably includes at least an aromatic diisocyanate, phosgene and hydrogen chloride, is preferably largely freed from the formed aromatic diisocyanate. This can be carried out in one stage (e.g., by selective condensation in an inert solvent, as has already been recommended for other gas phase phosgenation processes (EP-A-0 749 958)).

The condensation is preferably carried out however by spraying one or more suitable liquid streams (quench liquids) into the gas mixture leaving the reactor/reaction zone. In this way, a rapid cooling of the gas mixture can be carried out as described in EP-A-1 403 248, without using cold surfaces. Regardless of the type of cooling that is chosen, the temperature of the cooling zone is however preferably chosen so that (1) it is above the decomposition temperature of the carbamyl chlorides corresponding to the aromatic diisocyanate, and (2) the aromatic diisocyanate and possibly the solvent co-used as diluent in the amine vapor stream and/or phosgene stream condense or dissolve in the solvent, while excess phosgene, hydrogen chloride and possibly inert gas co-used as diluent pass through the condensation and quenching stage. For the selective separation of the aromatic diisocyanate from the gaseous mixture leaving the reactor/reaction zone, solvents maintained at a temperature of 80° to 200° C., preferably 80° to 180° C., such as for example chlorobenzene and/or dichlorobenzene, or aromatic diisocyanate or mixtures of the aromatic diisocyanate with chlorobenzene and/or dichlorobenzene are particularly suitable.

The generation of the flow of the gaseous reaction mixture essential for the process of the present invention, predominantly as a plug flow without any significant back mixing starting from the mixing zone through the reaction zone, is advantageously ensured by a pressure drop between the educt lines to the mixing zone on the one hand and the outlet from the condensation and quenching stage on the other hand. In general, the absolute pressure in the lines to the mixing zone is from 200 to 3000 mbar and behind the condensation and quenching stage is from 150 to 2500 mbar. The essential feature in this regard however is simply the maintenance of a differential pressure for the purposes of ensuring the above-described directed flow.

The gas mixture leaving the condensation and quenching stage is freed in step d) from residual isocyanate in a downstream gas wash with a suitable wash liquid, preferably inert solvents. Examples of suitable solvents include aromatic hydrocarbons with or without halogen substituents, such as chlorobenzene or o-dichlorobenzene. In a particularly preferred embodiment of the present invention, the solvent optionally used to dilute the educts and in the quenching stage, is then freed from excess phosgene in any manner known to those skilled in the art. This can be achieved by means of a cold trap, absorption in an inert solvent (e.g., chlorobenzene or dichlorobenzene), or by adsorption and hydrolysis on activated charcoal. Preferably, the absorption is carried out in an inert solvent with the resulting phosgene solutions being fed, preferably directly or after appropriate working-up, to a phosgene desorption unit, so that the phosgene used in excess is recycled for reuse. The hydrogen chloride gas passing through the phosgene recovery stage can be recycled in any manner known to those skilled in the art for the recovery of the chlorine required for the phosgene synthesis. The wash liquid occurring in step d) after its use for the gas wash is preferably employed in step c) as a quench liquid for cooling the gas mixture leaving the tubular reactor.

The purification of the aromatic diisocyanate(s) is then preferably carried out by distillative working-up of the solutions and mixtures obtained from the condensation and quenching stage.

Having thus described the invention, the following examples are given as being illustrative thereof. All parts and percentages given in these examples are parts by weight or percentages by weight, unless otherwise indicated.

EXAMPLES

Example 1

By mixing in a nozzle a mixture made up of gaseous 2,4- and 2,6-toluenediamine and phosgene, each of which was separately heated to above 300° C., was reacted adiabatically in a rotationally symmetrical tubular reactor with a residence time of less than 10 seconds (and more than 0.05 second). The gas mixture was passed through a condensation stage and was thereby cooled to a gas temperature of approximately 165° C. The condensate formed was fed to a distillation sequence and pure: TDI was obtained. The non-condensed gas mixture was washed with ortho-dichlorobenzene ("ODB") in a subsequent wash and the by-product HCl was separated absorptively from excess phosgene. The wash liquid was used in the condensation step.

The pressure difference between the pressure in the TDA line and at the head of the wash stage was 21 mbar, in order to achieve a directed gas flow from the lines.

The diamine mixture used was composed of 2,4- and 2,6-toluenediamine containing overall 0.01 mole % of aliphatic amines containing no keto groups, per mole of primary amino groups.

After an operating time of 300 hours, the differential pressure was 28 mbar and was thus unchanged within the limits of the measurement accuracy of industrial measuring instruments. An inspection showed no deposits of solids.

Example 2

Comparative

By mixing in a nozzle a mixture made up of gaseous 2,4- and 2,6-toluenediamine and phosgene, each of which was heated separately to a temperature above 300° C., was reacted adiabatically in a rotationally symmetrical tubular reactor with a residence time of less than 10 seconds (and more than 0.05 second). The gas mixture was then passed through a condensation stage and thereby cooled to a gas temperature of approximately 165° C. The condensate formed was fed to a distillation sequence and pure TDI was obtained. The non-condensed gas mixture was washed with ODB in a subsequent wash and the by-product HCl was separated absorptively from excess phosgene. The wash liquid was used in the condensation step.

The pressure difference between the pressure in the TDA line and at the outlet of the condensation stage was 50 mbar at the start of the experiment, in order to achieve a directed gas flow from the lines.

The mixture composed of 2,4- and 2,6-toluenediamine which was used contained 0.07 mole % overall of aliphatic amines containing no keto groups, per mole of primary amino groups.

After an operating time of 30 hours, the pressure in the gaseous TDA line rose significantly and the differential pressure between the TDA line and the outlet of the condensation stage was 3177 mbar. The reaction therefore had to be discontinued. An inspection revealed very large deposits of solids.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a primary aromatic diisocyanate comprising reacting a primary aromatic diamine with phosgene in gaseous phase in which
   a) the phosgene and the primary aromatic diamine are reacted within a mean residence time of 0.05 to 15 seconds, and
   b) the primary aromatic diamine contains less than 0.05 mole % overall of aliphatic amine containing no keto groups per mole of primary amino groups.

2. The process of claim 1 in which toluenediamine is the primary aromatic diamine.

3. The process of claim 1 in which the primary aromatic diamine is vaporized before the reaction and heated, optionally diluted with an inert gas or with vapors of an inert solvent, to a temperature of from 200° to 600° C., and the vaporized aromatic diamine contains substantially no droplets of non-vaporized aromatic diamine.

4. The process of claim 1 further comprising
   (i) continuously mixing the aromatic diamine in the vapor state, optionally diluted with an inert gas or with vapors of an inert solvent, and the phosgene which have been heated separately to a temperature of from 200° to 600° C. to obtain a reaction mixture,
   (ii) continuously leading the reaction mixture formed in (i) through a reaction zone while avoiding back mixing and wherein the phosgene and aromatic diamine are reacted in a mean residence time of 0.05 to 15 seconds to obtain a gas mixture,
   (iii) cooling the gas mixture from the reaction zone to a temperature above that of corresponding carbamyl chlorides' decomposition temperature to condense the aromatic diisocyanate, and
   (iv) separating non-condensed aromatic diisocyanate from the gas mixture by washing with a wash liquid.

5. The process of claim 4 in which (ii) is carried out adiabatically.

6. The process of claim 4 in which the reaction mixture produced in (i) is led through a reaction zone having a rotationally symmetrical geometry with a constant or increasing flow cross-sectional area in the reaction mixture's flow direction in (ii).

7. The process of claim 5 in which the reaction mixture produced in (i) is led through a reaction zone having a rotationally symmetrical geometry with a constant or increasing flow cross-sectional area in the reaction mixture's flow direction in (ii).

8. The process of claim 4 in which the gas mixture leaving the reaction zone comprises an aromatic diisocyanate, phosgene and hydrogen chloride, and is cooled in (iii) by spraying at least one liquid stream into the gas mixture.

9. The process of claim 8 in which at least a portion of the wash liquid from (iv) is used for cooling in (iii).

10. The process of claim 3 further comprising
  (i) continuously mixing the aromatic diamine in the vapor state, optionally diluted with an inert gas or with vapors of an inert solvent, and the phosgene which have been heated separately to a temperature of from 200° to 600° C. to obtain a reaction mixture,
  (ii) continuously leading the reaction mixture formed in (i) through a reaction zone while avoiding back mixing and wherein the phosgene and aromatic diamine are reacted in a mean residence time of 0.05 to 15 seconds to obtain a gas mixture,
  (iii) cooling the gas mixture from the reaction zone to a temperature above that of corresponding carbamyl chlorides' decomposition temperature to condense the aromatic diisocyanate, and
  (iv) separating non-condensed aromatic diisocyanate from the gas mixture by washing with a wash liquid.

11. The process of claim 10 in which (ii) is carried out adiabatically.

12. The process of claim 10 in which the reaction mixture produced in (i) is led through a reaction zone having a rotationally symmetrical geometry with a constant or increasing flow cross-sectional area in the reaction mixture's flow direction in (ii).

13. The process of claim 11 in which the reaction mixture produced in (i) is led through a reaction zone having a rotationally symmetrical geometry with a constant or increasing flow cross-sectional area in the reaction mixture's flow direction in (ii).

14. The process of claim 10 in which the gas mixture leaving the reaction zone comprises an aromatic diisocyanate, phosgene and hydrogen chloride, and is cooled in (iii) by spraying at least one liquid stream into the gas mixture.

15. The process of claim 14 in which at least a portion of the wash liquid from (iv) is used for cooling in (iii).

* * * * *